(12) United States Patent
Grass et al.

(10) Patent No.: US 6,438,194 B2
(45) Date of Patent: Aug. 20, 2002

(54) METHOD OF AND DEVICE FOR FORMING X-RAY IMAGES

(75) Inventors: Michael Grass, Hamburg (DE); Geerd Richard Kemkers, Fairfield, CT (US)

(73) Assignee: Koninklijke Philips Electronics. N.V., Eindhoven (NL)

( * ) Notice: Subject to any disclaimer, the term of this patent is extended or adjusted under 35 U.S.C. 154(b) by 0 days.

(21) Appl. No.: 09/761,250

(22) Filed: Jan. 16, 2001

(30) Foreign Application Priority Data

Jan. 18, 2000 (DE) ......................................... 100 01 709

(51) Int. Cl.[7] ................................................ A61B 6/03

(52) U.S. Cl. .................................. 378/4; 378/8; 378/15

(58) Field of Search ........................... 378/4, 8, 15, 20, 378/98, 12, 901

(56) References Cited

U.S. PATENT DOCUMENTS

| 5,647,360 A | * | 7/1997 | Bani-Hashemi et al. | .... 600/425 |
| 5,852,646 A | * | 12/1998 | Klotz et al. | ..................... 378/8 |
| 6,144,759 A | * | 11/2000 | Weese et al. | ............... 382/132 |

FOREIGN PATENT DOCUMENTS

EP        0860696 A2      8/1998

OTHER PUBLICATIONS

"Three–dimensional reconstruction of high contrast objects using C–arm image intensifier projection data" by M. Grass et al., in Computerized Medical Imaging and Graphics 23(1999) pp. 311–321.

* cited by examiner

Primary Examiner—David V. Bruce
(74) Attorney, Agent, or Firm—John Vodopia

(57) ABSTRACT

The invention relates to a method of forming X-ray images (B) from at least two series of projection data sets ($P_1$, $P_2$) successively acquired along different trajectories ($T_1$, $T_2$), a respective 3D data set ($S_1$, $S_2$) being formed from each series of projection data sets ($P_1$, $P_2$). In order to neutralize motions of the patient between the acquisition of the individual series of projection data sets upon combination of the 3D data sets so as to form X-ray images which are as free from artefacts as possible, the invention proposes to determine a transformation rule (F) describing the location in space of the 3D data sets ($S_1$, $S_2$) relative to one another in such a manner that voxels are selected in a 3D data set ($S_1$) and their location in the other 3D data set ($S_2$) is determined by means of a suitable similarity measure, after which X-ray images (B) are formed from the 3D data sets ($S_1$, $S_2$) combined by means of the transformation rule (F). Consequently, it is possible to dispense with phantom members that are to be reproduced for fine adjustment of the individual 3D data sets as well as with manual fine adjustment steps. The invention also relates to an X-ray device constructed for this purpose.

7 Claims, 2 Drawing Sheets

METHOD OF AND DEVICE FOR FORMING X-RAY IMAGES

BACKGROUND OF THE INVENTION

1. Field of the Invention

The invention relates to a method of forming X-ray images from at least two series of projection data sets successively acquired along different trajectories, a respective 3D data set being formed from each series of projection data sets. The invention also relates to an X-ray device which is particularly suitable for carrying out this method.

2. Description of the Related Art

A method and a device of this kind are known from EP 860 696 A2. Therein, two series of projection data sets are acquired along two semi-circular trajectories by means of a C-arm X-ray device, said trajectories extending at an angle of 60° relative to one another. Each series of projection data sets forms a respective 3D data set wherefrom a respective reconstruction image can be formed. Because a single 3D data set does not contain adequate data for a complete and correct reconstruction and artefacts occur during the reconstruction, the two (or more) 3D data sets are combined by weighted addition. The desired images are formed from the resultant data set by reconstruction; artefacts occur to a lesser extent in said images.

The acquisition of the series of projection data sets along the different trajectories normally takes place successively in time. For optimum compatibility of the projection data sets, or the 3D data sets to be formed therefrom, during the subsequent combination and reconstruction, it would be necessary for the object to be examined, for example a patient, to remain motionless during the data acquisition. In particular the position of the object to be examined should always be identical during the acquisition of the individual series of projection data sets and any translatory or rotary motions of the object to be examined should be as small as possible. However, because this can hardly be completely achieved during a practical examination of a patient, it is also known to reproduce, for example a phantom member in the X-ray images during the acquisition of the projection data sets; such a phantom can subsequently be used for fine adjustment so as to achieve matching 3D data sets. This operation is performed by a user.

SUMMARY OF THE INVENTION

Therefore, it is an object of the invention to provide a method which enables combination of 3D data sets without it being necessary for a user to perform a fine adjustment operation. It is also an object to provide an X-ray device which is suitably constructed for this purpose.

These objects are achieved by means of a method as disclosed in claim 1 and by means of an X-ray device as disclosed in claim 6.

The invention is based on the recognition of the fact that the same object to be examined is reproduced in all 3D data sets and that, therefore, individual structures can be traced in all 3D data sets. According to the invention this fact is used so as to select the voxel image values of at least one sub-volume in a first 3D data set and to search for these values in the other 3D data sets in order to derive therefrom a transformation rule describing a translatory or rotary motion, if any, occurring between the formation of individual 3D data sets. Generally speaking, the sub-volume $V_2$ is then selected automatically. The search in the other 3D data sets for voxels selected in a first 3D data set utilizes a suitable similarity measure for iteratively finding the corresponding voxel in the other 3D data sets.

Depending on the desired accuracy, this method can be performed with the appropriate number of voxels which should be distributed as well as possible throughout the entire volume represented by the 3D data set. The transformation rule or transformation rules found are then used to correct for motions of the object to be examined, to achieve quasi matching of the 3D data sets, to combine them so as to form a complete data set and to form the desired images therefrom. According to the method of the invention the foregoing can be realized without utilizing a phantom object or other markers reproduced in the X-ray images; the method can be performed automatically, that is, without interventions by a user.

In order to determine the transformation rule, several voxels located in respective sub-volumes of a 3D data set and/or individual voxels containing significant image information are advantageously selected in conformity with the claims 2 and 3.

Preferably, the functions indicated in claim 4 are used as a similarity measure. However, other possibilities are also feasible.

The method according to the invention is used primarily for a C-arm X-ray device, but can also be used in a computed tomography device; the invention can also be used notably in an X-ray device or a computed tomography device involving a conical X-ray beam.

Claim 6 discloses an X-ray device according to the invention which includes an X-ray source, an X-ray detector, a reconstruction unit and an arithmetic unit.

BRIEF DESCRIPTION OF THE DRAWINGS

The invention will be described in detail hereinafter with reference to the drawings. Therein.

DETAILED DESCRIPTION OF THE PREFERRED EMBODIMENT

Figure 1:
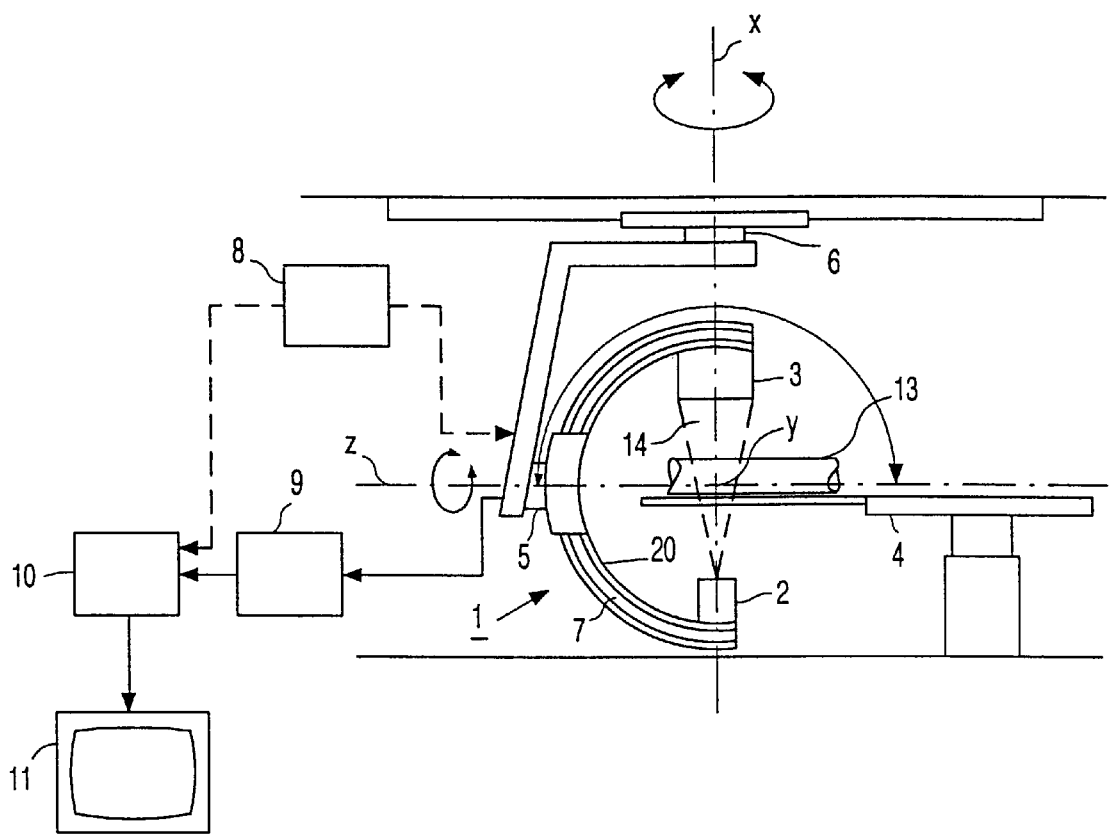
FIG. 1 shows a C-arm X-ray device according to the invention.

The C-arm X-ray device 1 shown in FIG. 1 includes an X-ray tube 2 which is mounted at one end of the C-arm 20 and an X-ray detector 3 which is mounted at the other end of the C-arm 20. The X-ray tube 2 produces a conical X-ray beam 14 which irradiates an object 13 to be examined, for example, a patient who is arranged on a patient table 4 in the examination zone, after which the beam is incident on the two-dimensional X-ray detector 3. The X-ray tube 2 and the X-ray detector 3 are rotatable about the y axis by way of rails 7 provided on the C-arm 20. Because of the suspension by means of a plurality of arms and links 5, 6, the position of the C-arm 20 can be changed in different directions; for example, the C-arm 20 is capable of rotation about the x, the y and the z axis.

Such motions for the acquisition of projections from different X-ray positions and the data acquisition are controlled by means of a control unit 8. The projections acquired are applied to a reconstruction unit 9 which forms a respective 3D data set, and possibly therefrom a reconstruction image, from a series of projections acquired along a trajectory. Such 3D data sets, or the reconstruction images, are subsequently applied to an arithmetic unit 10 which determines the transformation rules (or the transformation parameters for a transformation) between the individual 3D data sets in conformity with the method of the invention and ultimately forms the desired X-ray images from the 3D data sets by means of the transformation rules; the desired X-ray images can be displayed on a monitor 11.

Figure 2:
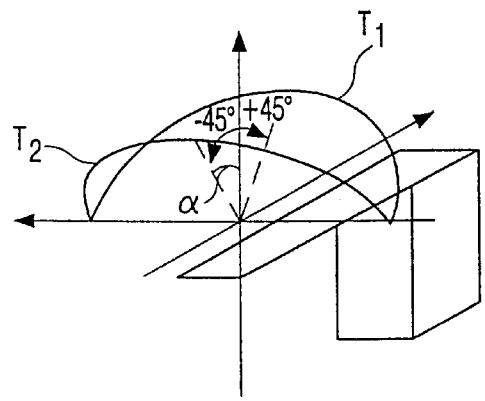
FIG. 2 illustrates two trajectories.

FIG. 2 shows a sketch illustrating two trajectories $T_1$ and $T_2$. Each trajectory describes the path traveled by the center of the detector surface of the X-ray detector 3 during the acquisition of projection data sets. The trajectory is, therefore, the curve extending through all X-ray positions in which a respective projection is acquired. In the case shown the trajectories $T_1$ and $T_2$ describe a respective semi-circle and are tilted through an angle of $2\alpha = 90°$ relative to one another. A first 3D data set is acquired from the projections acquired along the trajectory $T_1$ whereas a second 3D data set is formed from the projections acquired along the trajectory $T_2$. In order to match these data sets, that is, in order to eliminate any translatory or rotary motion of the patient occurring between the acquisition of the first and the second series of projections, the transformation rule between the two 3D data sets is subsequently determined as will be described in detail hereinafter with reference to FIG. 3.

Figure 3:
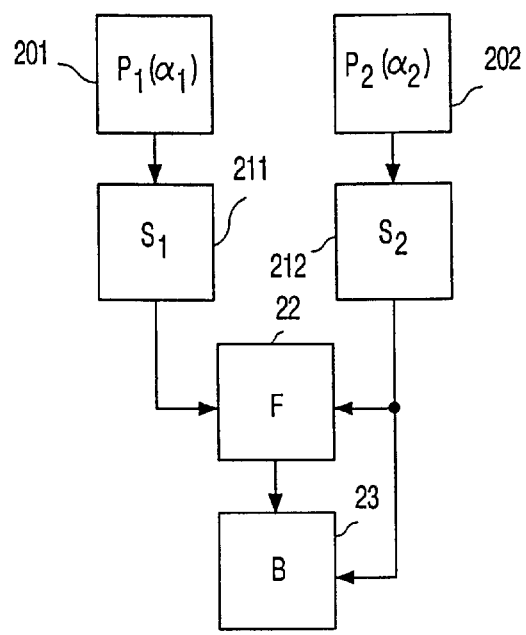
FIG. 3 shows a block diagram illustrating the method according to the invention.

In the block diagram shown in FIG. 3 two sets of projections $P_1(\alpha_1)$ and $P_2(\alpha_2)$ are symbolically shown as starting points in the blocks 201 and 202; these two sets have been acquired along two trajectories $T_1$ and $T_2$ extending at angles $\alpha_1$ and $\alpha_2$, respectively, relative to a reference plane. In the blocks 211 and 212 a respective 3D data set $S_1$, $S_2$ is formed from each of the projection data sets $P_1$, $P_2$.

Subsequently, in the block 22 a transformation rule is determined from the two 3D data sets $S_1$, $S_2$ and is applied to one (or both) of the two data sets (for example to $S_1$).

The transformation rule is derived, for example, as follows:

a) The voxels (for example, 16×16×16) of a sub-volume $V_1$ (that is, a part of the volume reproduced by the 3D data set) are selected from one of the two 3D data sets, for example the data set $S_1$. This selection can be performed automatically, for example, by selecting a sub-volume having an as high as possible contrast (where the voxel image values in the sub-volume deviate as much as possible from their mean value).

b) Subsequently, the co-ordinates $x_1$ of the voxels in the sub-volume $V_1$ are subjected to a transformation, for example in conformity with the relation:

$$X_2 = \Re(X_1 - U) + \bar{t} \quad (1)$$

where $x_1$, $x_2$, u, t are vectors and $\Re$ is a rotation matrix which describes in the transformation of the co-ordinates upon a rotation of the co-ordinate system about its origin. Only the vector $x_1$ from among the vectors is known (this is the vector which connects the voxel to the co-ordinate origin). The vector u represents the co-ordinates of the point around which the rotation takes place and t is a vector corresponding to the translation of the voxel. The resultant vector $x_2$ represents the co-ordinates of the voxel in the volume represented by the second 3D data set. When the transformation is applied to all voxels of the sub-volume, an equally large sub-volume $V_2$ will be obtained in the second data set $S_2$.

c) Subsequently, the correspondence between the voxel image values of the sub-volume $V_2$ and the voxel image values of the sub-volume $V_1$ of the first 3D data set $S_1$ is evaluated by way of a similarity measure. Subsequently, the position and/or the orientation of the sub-volume selected in the second data set is varied (by varying u, t, or ) and the similarity between this sub-volume and the sub-volume $V_1$ is again evaluated by way of the similarity measure. These steps are iteratively repeated until the sub-volume which exhibits the best correspondence to the sub-volume $V_1$ of the 3D data set $S_1$ is found from the 3D data set $S_2$. The associated transformation parameters (u, t, or $\Re$) then define the transformation rule.

For example, the mean absolute difference MAD of the voxel image values in the two volumes can be taken as the similarity measure:

$$MAD = \frac{1}{n} \sum_{i=1}^{n} (V_{1i} - V_{2i})$$

where n is the number of voxels in the sub-volume $V_1$ or $V_2$, and $V_{1i}$ and $V_{2i}$ are the $i^{th}$ voxel image value in the first sub-volume $V_1$ and in the second sub-volume $V_2$, respectively. Instead of minimizing the mean absolute difference, for example, the root of the square differences can also be minimized or the similarity can be evaluated by means of a suitable correlation coefficient (for example, for a cross-correlation, double correlation or the Pearson linear correlation).

The extraction of the transformation parameters from a sub-volume requires less calculation time than if these parameters were determined while utilizing all voxel image values of the 3D data sets. However, it is less accurate and more influenced by noise. The accuracy can be improved by taking into account two or more sub-volumes for each 3D data set and by averaging the transformation parameters found for the various sub-volumes.

The described transformation is based on the assumption that a rigid object to be examined is present in the examination zone. The object, however, could also be deformable. The location-dependent transformation parameters could then be determined by means of a so-called "elastic matching" method.

In the block 23 an improved 3D data set S is determined from the transformed 3D data set $S_1$ and from $S_2$ by way of preferably weighted summing of the voxel image values of voxels which correspond to one another in conformity with the transformation. As the weighting factor whereby a voxel image value is multiplied is greater, its distance from the plane defined by the associated trajectory $T_1$ or $T_2$ will be smaller (and vice versa) and the less the noise and the artefacts will be. This is because the artefacts in the two 3D data sets $S_1$ and $S_2$ become more manifest in the voxels which are situated comparatively far from said plane.

Figure 4:
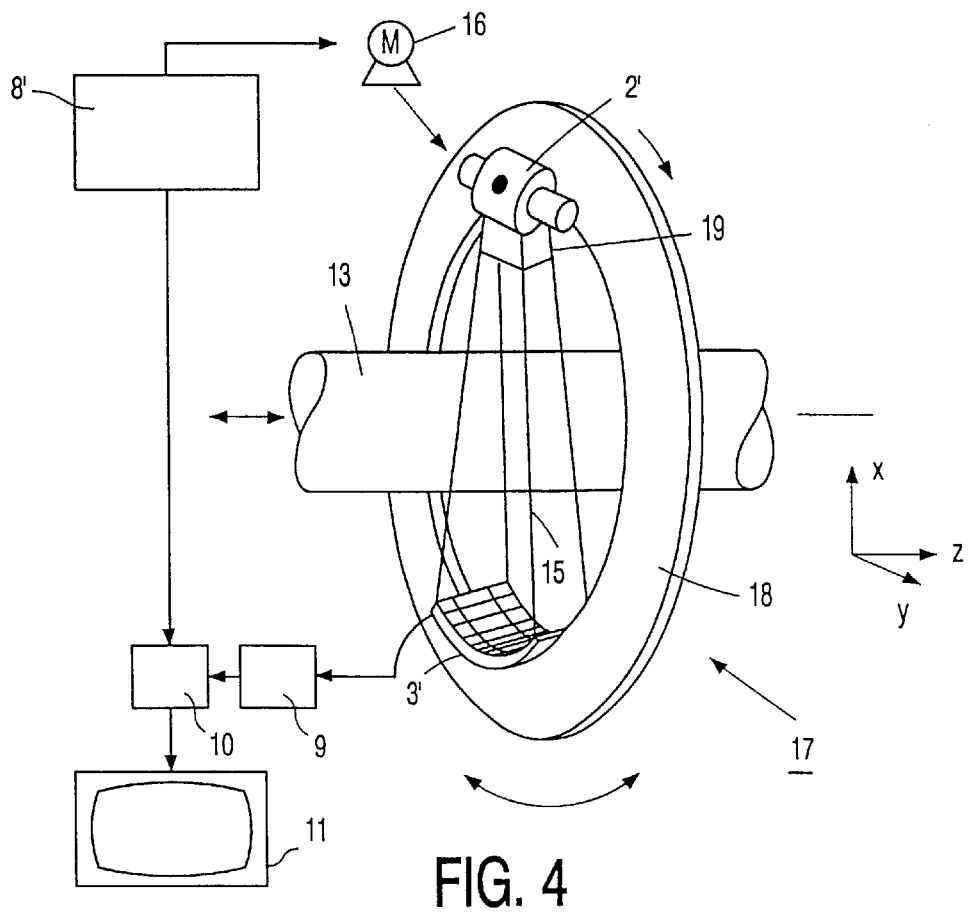
FIG. 4 shows a computed tomography device constructed in accordance with the invention.

FIG. 4 shows a computed tomography device according to the invention. The X-ray source 2' with a collimator 19 for producing a conical X-ray beam 15 and the X-ray detector 3' are mounted on a ring-shaped gantry 18; for the acquisition of projections they rotate around the object 13 to be examined which is arranged along the z axis. To this end, the gantry 18 is driven by a motor drive 16 which itself is controlled by a control unit 8'. The projections acquired are applied to a reconstruction unit 9 for the formation of 3D data sets and reconstruction images which are applied to the arithmetic unit 10 again. The formation of the transformation rule and the subsequent formation of X-ray images take place in conjunction with the C-arm X-ray device 1 as described above and, therefore, will not be described again.

The X-ray devices shown are merely examples of embodiments of the invention. The invention can also be used in other X-ray devices wherein a complete data set is to be formed from a plurality of 3D data sets and X-ray images are to be formed therefrom. The trajectories and their number as shown in FIG. 2 are also given merely by way of example. The projections can also be acquired along other trajectories or along more than two trajectories, for example along two or more parallel full circles or two full circles extending perpendicularly to one another.

What is claimed is:

1. A method of forming X-ray images (B) from at least two series of projection data sets successively acquired along different trajectories, a respective 3D data set being formed from each series of projection data sets and a transformation rule, describing the location in space of the 3D data sets relative to one another, being determined in that voxels in one 3D data set are selected and their location in the other 3D data set is determined by means of a suitable similarity measure, and X-ray images being formed from the 3D data sets combined by way of the transformation rule.

2. A method as claimed in claim 1, wherein a plurality of voxels are selected in each time a sub-volume of a 3D data set in order to determine the transformation rule.

3. A method as claimed in claim 1, wherein individual sub-volumes containing significant image information are selected in order to determine the transformation rule.

4. A method as claimed in claim 1, wherein the mean absolute difference, the mean square difference, the double correlation or the Pearson linear correlation is used as the similarity measure.

5. A method as claimed in claim 1, wherein the projection data sets are acquired by means of a C-arm X-ray device or a computed tomography device.

6. An X-ray device, notably for carrying out the method claimed in claim 1, which includes an X-ray source and an X-ray detector for the acquisition of a plurality of series of projection data sets along different trajectories around an object to be examined, a reconstruction unit for forming 3D data sets from respective series of projection data sets, and an arithmetic unit which is constructed in such a manner that a transformation rule describing the location in space of the 3D data sets relative to one another is determined by selecting voxels in a 3D data set and by determining their location in the other 3D data set by means of a suitable similarity measure, X-ray images being formed from the 3D data sets combined by way of the transformation rule.

7. An X-ray device as claimed in claim 6, wherein the X-ray device is a C-arm X-ray device or a computed tomography device.

* * * * *